US010799693B2

(12) United States Patent
Ueda et al.

(10) Patent No.: US 10,799,693 B2
(45) Date of Patent: *Oct. 13, 2020

(54) CONNECTOR

(71) Applicant: Terumo Kabushiki Kaisha, Shibuya-ku, Tokyo (JP)

(72) Inventors: Yasuhiro Ueda, Yamanashi (JP); Yasunobu Zushi, Yamanashi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/040,789

(22) Filed: Jul. 20, 2018

(65) Prior Publication Data

US 2018/0326199 A1  Nov. 15, 2018

Related U.S. Application Data

(63) Continuation of application No. 13/876,747, filed as application No. PCT/JP2011/071948 on Sep. 27, 2011, now Pat. No. 10,046,157.

(30) Foreign Application Priority Data

Sep. 28, 2010  (JP) .................................. 2010-217068

(51) Int. Cl.
*A61M 39/22* (2006.01)
*A61M 39/04* (2006.01)
(Continued)

(52) U.S. Cl.
CPC .......... *A61M 39/22* (2013.01); *A61M 39/045* (2013.01); *A61M 39/26* (2013.01);
(Continued)

(58) Field of Classification Search
CPC .... A61M 39/22; A61M 39/045; A61M 39/26; A61M 2039/0036; A61M 2039/1083; A61M 2039/1088; A61M 2039/2433
See application file for complete search history.

(56) References Cited

U.S. PATENT DOCUMENTS 5,114,408 A * 5/1992 Fleischhaker ..... A61M 39/0606
604/167.04
6,171,287 B1 * 1/2001 Lynn ..................... A61M 39/02
251/149
(Continued)

FOREIGN PATENT DOCUMENTS

CN           1390286 A      1/2003
CN         101318055 A     12/2008
(Continued)

OTHER PUBLICATIONS

International Search Report (PCT/ISA/210) dated Nov. 15, 2011, by the Japanese Patent Office as the International Searching Authority for International Application No. PCT/JP2011/071948.
(Continued)

*Primary Examiner* — Theodore J Stigell
(74) *Attorney, Agent, or Firm* — Buchanan Ingersoll & Rooney PC

(57) ABSTRACT

A connector of the present invention includes a housing and a valve, wherein the housing has a flow path and a pipe connecting port, and the valve is formed of an elastic material and is adapted to block the pipe connecting port. The valve has a substantially columnar deformable portion. The deformable portion has a top surface exposed from the pipe connecting port, a bottom surface opposite to the top surface, and a slit that reaches extends from the top surface to the bottom surface. When the top surface is pressed by the pipe, the deformable portion of the valve will be displaced toward the flow path while elastically deforming, so that
(Continued)

inner surfaces that define the slit will face the flow path, and the top surface will form an opening that communicates with the flow path.

17 Claims, 5 Drawing Sheets

(51) Int. Cl.
*A61M 39/26* (2006.01)
*A61M 39/00* (2006.01)
*A61M 39/10* (2006.01)
*A61M 39/24* (2006.01)

(52) U.S. Cl.
CPC .............. *A61M 2039/0036* (2013.01); *A61M 2039/1083* (2013.01); *A61M 2039/1088* (2013.01); *A61M 2039/2433* (2013.01); *Y10T 29/49826* (2015.01)

(56) References Cited

U.S. PATENT DOCUMENTS

| | | | | |
|---|---|---|---|---|
| 6,808,161 | B1 * | 10/2004 | Hishikawa | A61M 39/045 251/149.1 |
| 10,046,157 | B2 * | 8/2018 | Ueda | A61M 39/22 |
| 2003/0208165 | A1 * | 11/2003 | Christensen | A61M 39/045 604/256 |
| 2006/0111694 | A1 * | 5/2006 | Fukai | A61M 39/045 604/403 |
| 2006/0184140 | A1 * | 8/2006 | Okiyama | A61M 39/045 604/249 |
| 2008/0306469 | A1 * | 12/2008 | Masuda | A61M 39/22 604/535 |
| 2015/0190623 | A1 * | 7/2015 | Ueda | A61M 39/1011 604/246 |

FOREIGN PATENT DOCUMENTS

| | | |
|---|---|---|
| EP | 1550478 A1 | 7/2005 |
| EP | 1894598 A1 | 3/2008 |
| EP | 2042214 A1 | 4/2009 |
| JP | 2002-516160 A | 6/2002 |
| JP | 2004-195180 A | 7/2004 |
| WO | WO 2008/043069 A2 | 4/2008 |
| WO | WO 2010/073643 A1 | 7/2010 |

OTHER PUBLICATIONS

Office Action dated Jul. 29, 2014 issued by the Chinese Patent Office in corresponding Chinese Patent Application No. 201180035505.6, with English-language translation (11 pages).

* cited by examiner

CONNECTOR

CROSS REFERENCE TO RELATED APPLICATIONS

This application is a continuation of U.S. application Ser. No. 13/876,747 having a filing date of May 31, 2013, which is a U.S. national stage application based on International Application No. PCT/JP2011/071948 filed on Sep. 27, 2011, which claims priority to Japanese Application No. 2010-217068 filed on Sep. 28, 2010, the entire content of all three of which is incorporated herein by reference.

TECHNICAL FIELD

The present invention relates to a connector capable of liquid-tightly connecting a pipe of various medical instruments, infusion containers or the like, for example.

BACKGROUND ART

Conventionally, when performing fluid infusion, blood transfusion, hemodialysis or the like, the liquid is infused into the body by using a medical tube. Further, in the case where another liquid (such as a medical solution or the like) is to be merged into the liquid within the tube, a connector capable of liquid-tightly connecting a pipe of a syringe, a luer taper member or the like is used.

An example of such connector is disclosed in Japanese Unexamined Patent Application Publication (Translation of PCT Application) No. 2002-516160. The connector disclosed in this Japanese application publication includes a housing to which the pipe can be connected, and a valve arranged in the housing. The housing is provided with a flow path through which the liquid sent by the tube passes, and an opening which communicates with the flow path. The opening of the housing is blocked by a valve.

The valve is made of an elastic material, and has a slit-like insertion hole. The slit-like insertion hole of the valve is closed in the normal state, and no cavity is formed in the valve (i.e., the valve has a non-dead shape). Thus, the valve can liquid-tightly connect the pipe of the luer taper member or the like. On the other hand, when the pipe is connected to the connector, the valve will be pressed by the pipe and thereby deform, so that the slit-like insertion hole is opened. Thus, the pipe is brought into communication with the housing, so that another liquid (such as a medical solution or the like) is infused from the pipe. In the aforesaid configuration, the valve has a shape that is less susceptible to drug accumulation.

SUMMARY

However, in the connector disclosed in Japanese Unexamined Patent Application Publication No. 2002-516160, since the tip end of the pipe is inserted into the flow path, the tip end of the pipe contacts the liquid in the flow path, and therefore if the tip end of the pipe has bacteria adhering thereon, the liquid in the flow path will be contaminated.

Further, when the elastic portion of the valve deforms, the insertion hole will expand to become a bag-like shape, so that a space will be formed in the valve. As a result, liquid will accumulate in the valve.

The connector disclosed here is configured so that even if the tip end of the pipe is not inserted into the flow path of the housing, the valve thereof can be opened without causing liquid accumulation in the valve.

The connector according to an aspect of the disclosure includes a housing and a valve.

The housing has a flow path through which a liquid passes, and a pipe connecting port which communicates with the flow path.

The valve is formed of an elastic material and adapted to block the pipe connecting port of the housing. The valve has a deformable portion and a fixing piece, wherein the deformable portion has a top surface exposed from the pipe connecting port, a bottom surface opposite to the top surface, and a slit reaching from the top surface to the bottom surface. The fixing piece is formed in an intermediate portion between the top surface and the bottom surface, and is fixed to the housing. When the top surface is pressed by the pipe, the deformable portion will elastically deform, so that inner surfaces which define the slit face the flow path of the housing, and the top surface forms an opening which communicates with the flow In the connector having the aforesaid configuration, when the pipe is connected to the pipe connecting port of the housing, the top surface of the deformable portion of the valve will be pressed by the pipe. Thus, the deformable portion elastically deforms, so that the inner surfaces that define the slit of the deformable portion rotate to face the flow path of the housing. Further, the top surface forms the opening that communicates with the flow path.

As a result, the pipe comes into communication with the flow path of the housing through the opening formed by the top surface of the valve. Thus, the tip end of the pipe will never be inserted into the flow path. Further, the path extending from the tip end of the pipe to the flow path of the housing can be reduced, and space will not (or less likely) be formed in the valve. Thus, the liquid can be prevented or hindered from being accumulated in the valve.

With the connector having the aforesaid configuration, even if the tip end of the pipe is not inserted into the flow path of the housing, the valve can be opened. Further, even if the valve is pressed by the pipe to deform, space will not (or less likely) be formed in the valve, and therefore liquid can be prevented or hindered from being accumulated in the valve.

BRIEF DESCRIPTION OF DRAWING FIGURES

Figure 5:
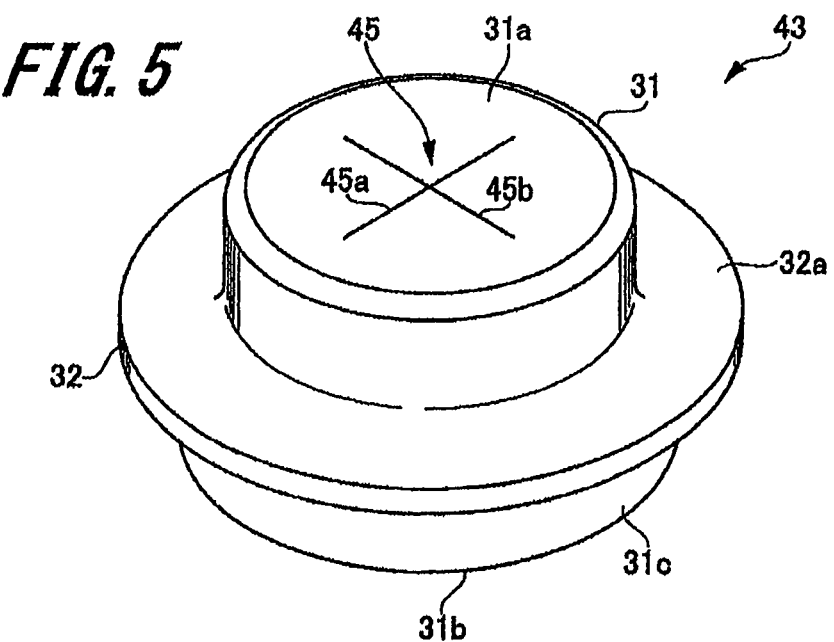
Figure 6:
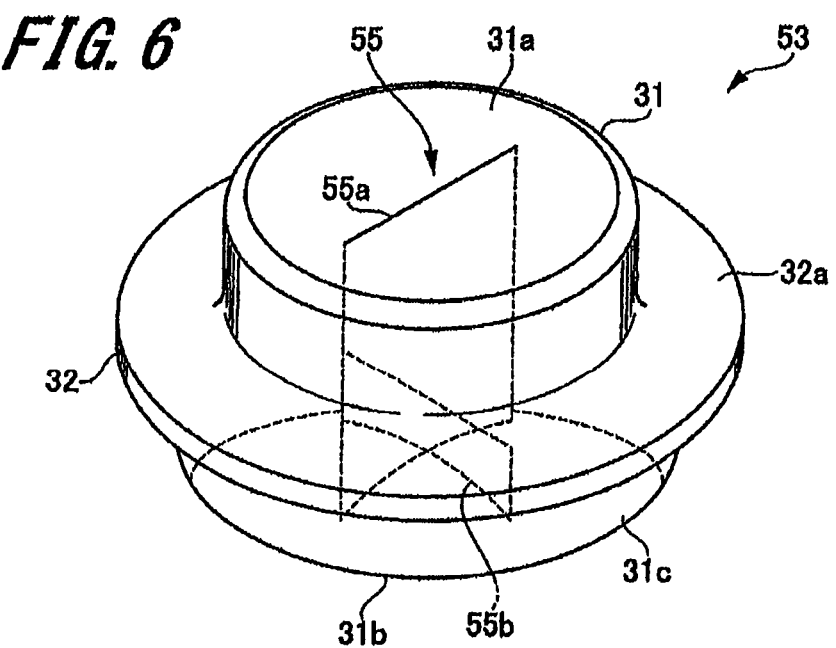
Figure 7A:
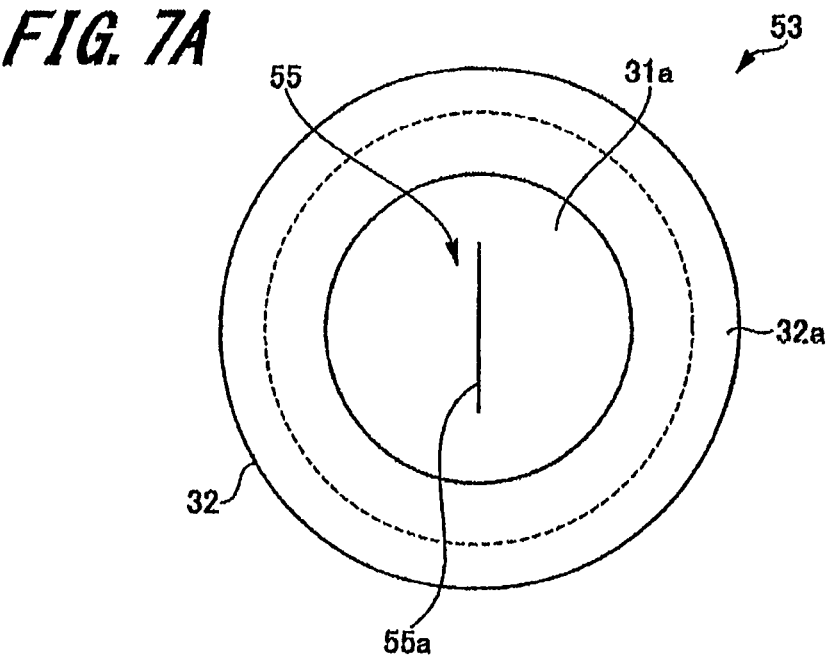
Figure 7B:
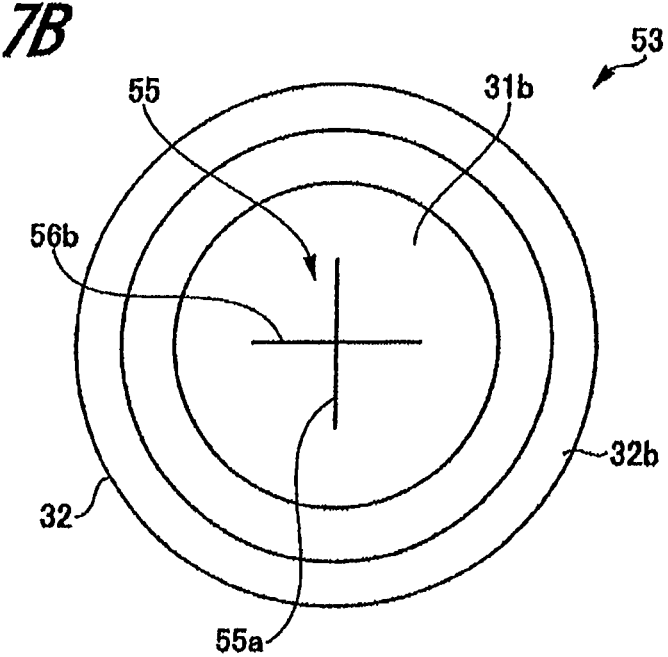

FIG. 4A is a cross-sectional view showing a state in which a pipe is caused to face the connector according to the first embodiment, FIG. 4B is a cross-sectional view showing a state in which a top surface of the valve of the connector according to the first embodiment is pressed by the pipe, and FIG. 4C is a cross-sectional view showing a state in which the pipe is connected to the connector according to the first embodiment;

FIG. 5 is a perspective view showing a valve of a connector according to a second embodiment of the present invention;

FIG. 6 is a perspective view showing a valve of a connector according to a third embodiment of the present invention; and FIG. 7A is a plan view of the valve of the connector according to the third embodiment, and FIG. 7B is a bottom view of the valve of the connector according to the third embodiment.

DETAILED DESCRIPTION

Embodiments of the connector according to the present invention will be described below with reference to FIGS. 1 to 5. Note that, in the drawings, the same components are denoted by the same reference numerals. Further, the present invention is not limited to the embodiments described below.

1. First Embodiment

[Configuration Example of Connector]

First, a connector according to a first embodiment of the present invention will be described below with reference to FIG. 1.

Figure 1:
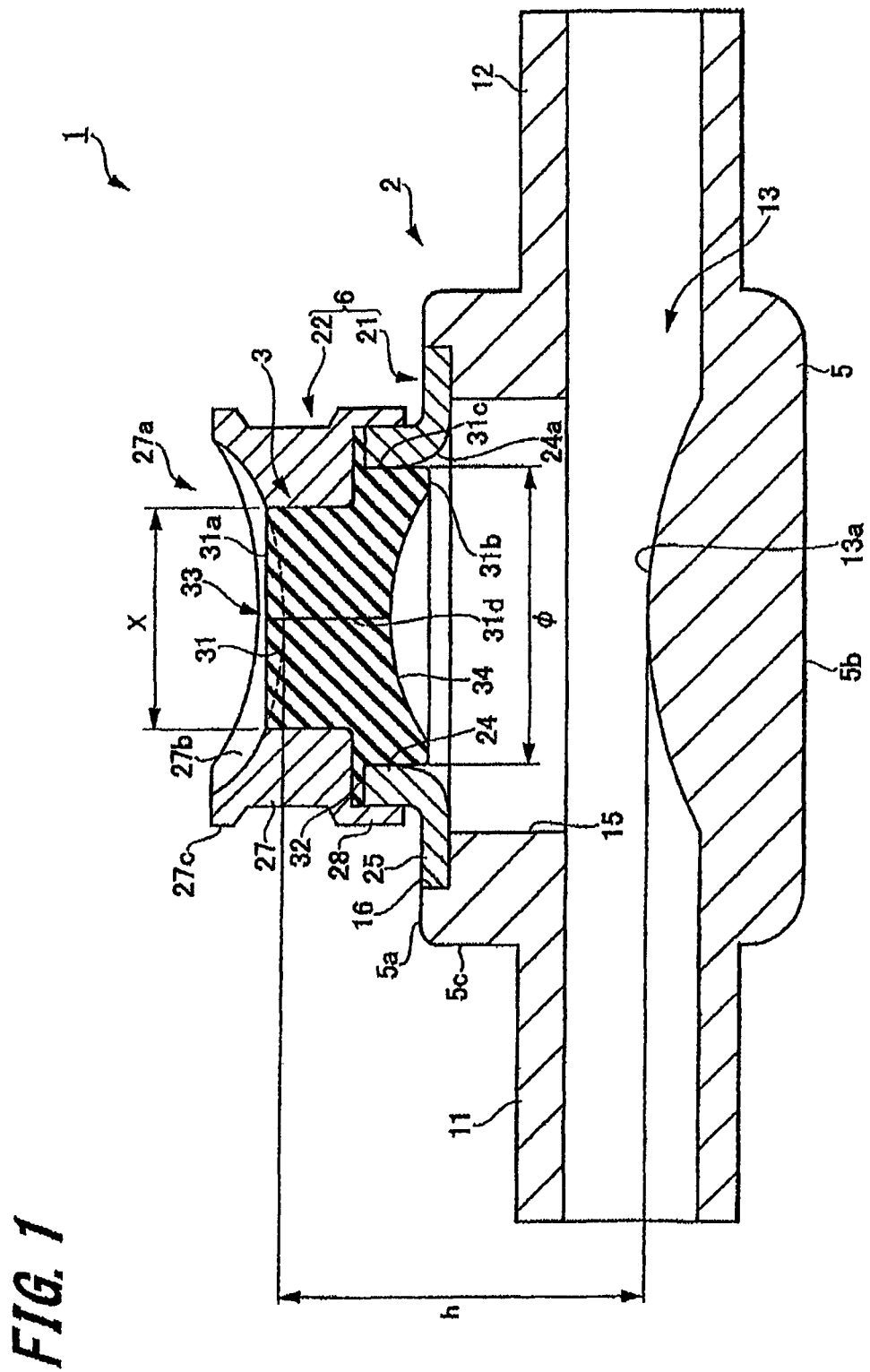
FIG. 1 is a cross-sectional view showing a connector according to a first embodiment of the present invention.

FIG. 1 is a cross-sectional view showing a connector 1 of the first embodiment.

As shown in FIG. 1, the connector 1 includes a housing 2, and a valve 3 fixed to the housing 2.

[Housing]

Examples of the material of the housing 2 include polyolefins such as polyethylene, polypropylene, ethylene-propylene copolymers, and ethylene-vinyl acetate copolymers (EVA) and the like, polyvinyl chloride, polyvinylidene chloride, polystyrene, polyimide, polyimide, polyimide-imide, polycarbonate, poly(4-methylpentene-1), ionomers, acrylic resins, polymethyl methacrylate, acrylonitrile-butadiene-styrene copolymer (ABS resin), acrylic-styrene copolymers (AS resins), butadiene styrene copolymers, polyesters such as polyethylene terephthalate (PET), polybutylene terephthalate (PBT), polycyclohexane terephthalate (PCT), polyether, polyether ketone (PEK), polyether ether ketone (PEEK), polyether imide, polyacetal (POM), polyphenylene oxide, denatured polyphenylene oxide, polysulfone, polyether sulfone, polyallylate, polyphenylene sulfide, polyarylate, aromatic polyester (liquid crystal polymers), polytetrafluoroethylene, polyvinylidene fluoride, and other fluororesins, a blended material or a polymer alloy each having at least one of the aforesaid materials as a component thereof. Examples of the material of the housing 2 also include various kinds of glass materials, ceramic materials, and metallic materials.

The housing 2 includes a housing main body 5, and a pipe connecting port 6 joined to the housing main body 5. The housing main body 5 is a substantially columnar hollow casing, and has an upper surface 5a, a lower surface 5b, and an outer peripheral surface 5c, wherein the upper surface 5a is one end in the axial direction, and the lower surface 5b is the other end.

A first tube connecting port 11 and a second tube connecting port 12 are arranged on the outer peripheral surface 5c of the housing main body 5. The tube connecting ports 11, 12 are each formed in a cylindrical shape protruding from the outer peripheral surface 5c of the housing main body 5. Both the axis of the first tube connecting port 11 and the axis of the second tube connecting port 12 coincide with the radial direction of the housing main body 5.

A flow path 13 extending from the first tube connecting port 11 to the second tube connecting port 12 is provided in the housing main body 5. In other words, the flow path 13 extends in the radial direction of the housing main body 5.

A through-hole 15 which communicates with the flow path 13 is formed in the upper surface 5a of the housing main body 5. A bottom surface 13a of the flow path 13, which faces the through-hole 15, is formed in a convex shape. A circular fitting recess 16 is formed around the through-hole 15 of the upper surface 5a of the housing main body 5. A first member 21 (which is to be described later) of the pipe connecting port 6 is fitted into the fitting recess 16.

The pipe connecting port 6 includes the aforementioned first member 21, and a second member 22, wherein the first member 21 is joined to the housing main body 5, and the second member 22 is joined to the first member 21. The pipe connecting port 6 communicates with the flow path 13 of the housing 2.

The first member 21 forms a base end of the pipe connecting port 6. The first member 21 includes a tubular portion 24 and a flange portion 25. A fixing piece 32 (which is to be described later) of the valve 3 abuts one end face of the tubular portion 24 in the axial direction. A curved surface 24a is formed on the inner surface of the tubular portion 24, wherein the inner diameter of the curved surface 24a becomes larger as it goes toward the other end of the tubular portion 24.

The flange portion 25 is continuous with the other end of the tubular portion 24, and is formed in a ring-like shape protruding outward in the radial direction of the tubular portion 24. The outer diameter of the flange portion 25 is substantially equal to the diameter of the fitting recess 16 of the housing main body 5. The flange portion 25 is fitted into the fitting recess 16 so as to be joined to the housing main body 5. Incidentally, the flange portion 25 may also be joined to the housing main body 5 by other fixing methods such as adhesive, fusion and the like.

The second member 22 forms a tip end of the pipe connecting port 6. The second member 22 includes a pipe fitting portion 27 and a connection piece 28, wherein the pipe fitting portion 27 is to be fitted by a pipe 100 (see FIGS. 4A, 4B and 4C), and the connection piece 28 is continuous with the pipe fitting portion 27.

The pipe fitting portion 27 is formed substantially in a cylindrical shape, and has a tube hole 27a. A curved surface (tapered surface) 27b is formed on the inner surface of the pipe fitting portion 27, wherein the inner diameter of the curved surface 27b becomes larger as it goes toward one end of the pipe fitting portion 27. Thus, it is possible to easily insert the pipe 100 into the pipe fitting portion 27 of the pipe connecting port 6.

The fixing piece 32 of the valve 3 abuts the other end of the pipe fitting portion 27. In other words, the pipe connecting port 6 fixes the valve 3 by sandwiching the fixing piece 32 of the valve 3 between the one end of the tubular portion 24 and the other end of the pipe fitting portion 27.

Further, a screw portion 27c is arranged on the outer peripheral surface of the pipe fitting portion 27. The screw portion 27c is adapted to be screwed with a lock portion (so-called "luer lock", which is not shown in the drawings) formed around the pipe 100 at a predetermined interval.

The connection piece 28 is arranged on the outer peripheral surface of the pipe fitting portion 27 on the side of the other end, and is formed in a cylindrical shape whose inner diameter is greater than the inner diameter of the pipe fitting portion 27. The inner diameter of the connection piece 28 is substantially equal to the outer diameter of the tubular portion 24 of the first member 21. The connection piece 28 is fitted and joined to the tubular portion 24 of the first member 21. Incidentally, the connection piece 28 may also be joined to the first member 21 by other fixing methods such as adhesive, fusion and the like. When the connection piece 28 is joined to the tubular portion 24 of the first member 21, the fixing piece 32 of the valve 3 will be pressed by the one end of the tubular portion 24 and the other end of the pipe fitting portion 27 so as to be crushed.

Next, the dimensions of the housing 2 will be described below.

The diameter X of the tube hole 27a of the pipe fitting portion 27 is determined according to the size of the upper portion of a deformable portion 31 (which is to be described later) of the valve 3. The diameter X of the tube hole 27a will be described in more detail later when discussing the dimensions of the valve 3. Further, it is preferred that the distance h between the lower edge of the curved surface 27b and the bottom surface 13a of the flow path 13 is set within a range of 5 to 15 mm.

The diameter φ of the tubular portion 24 is determined according to the size of the lower portion of the deformable portion 31 of the valve 3, and is preferably equal to or larger than 4 mm. The tube hole of the tubular portion 24, whose diameter is φ, is a space necessary for the valve 3 to elastically deform (which is to be described later). Incidentally, the diameter φ may be at least partially equal to or larger than 4 mm. For example, in the case where the inner diameter of tube hole of the tubular portion 24 is continuously reduced as it goes toward the flow path 13, the diameter of the tube hole of the tubular portion 24 on the side of the pipe fitting portion 27 may be equal to or larger than 4 mm.

[Valve]

Next, the valve 3 will be described below with reference to FIGS. 2 and 3.

Figure 2:
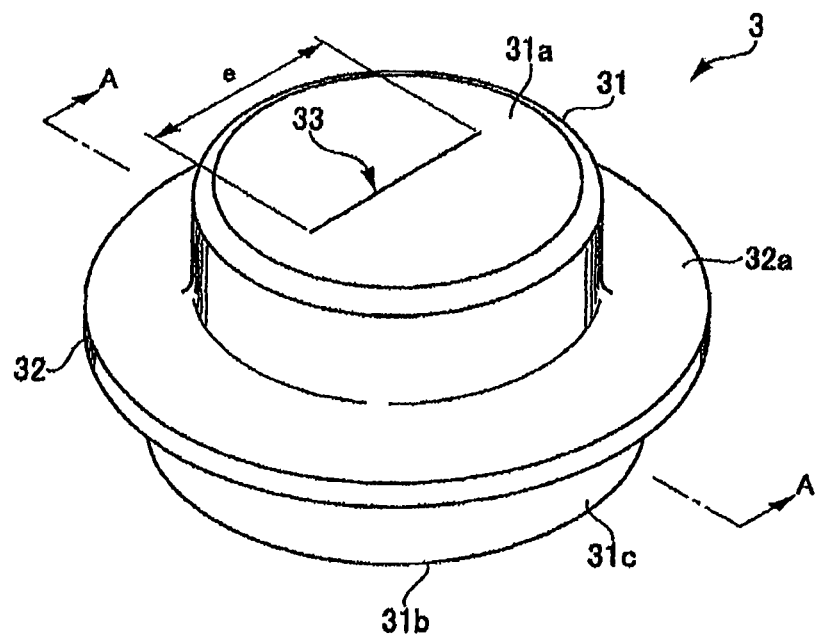
FIG. 2 is a perspective view showing a valve of the connector according to the first embodiment.
Figure 3:
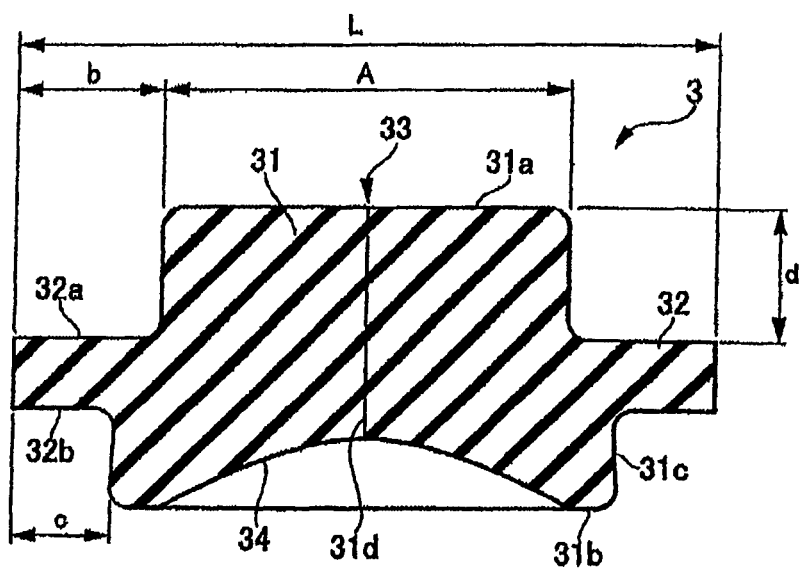
FIG. 3 is a cross section taken along line A-A of FIG. 2.

FIG. 2 is a perspective view of the valve, and FIG. 3 is a cross section taken along line A-A of FIG. 2.

The valve 3 is formed of an elastic material, so as to be elastically deformable. Examples of the material of the valve 3 include various kinds of rubber such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, various kinds of thermoplastic elastomers such as a styrene-based elastomer, a polyolefine-based elastomer, a polyvinyl chloride-based elastomer, a polyurethane-based elastomer, a polyester-based elastomer, a polyimide-based elastomer, a polybutadine-based elastomer, and a fluorocarbon rubber-based elastomer. Examples of the material of the valve 3 also include a blended material having one, two or more of the aforesaid materials as the component thereof.

Further, it is preferred that the hardness of the valve 3 is 20° to 60° (hardness A). Thus, since suitable elastic force of valve 3 can be ensured, it is possible for the valve 3 to elastically deform (which is to be described later).

As shown in FIGS. 2 and 3, the valve 3 includes the deformable portion 31 where a slit 33 is formed, and the fixing piece 32 arranged in the deformable portion 31.

The deformable portion 31 is formed in a shape in which two columns having the same axis but different diameters are continuous with each other in the axial direction; and the deformable portion 31 has a top surface 31a, a bottom surface 31b, and an outer peripheral surface 31c, wherein the top surface 31a is one end in the axial direction, and the bottom surface 31b is the other end (i.e., the end opposite to the top surface 31a) in the axial direction.

The upper portion of the deformable portion 31 where the top surface 31a is formed is inserted into the tube hole 27a of the pipe fitting portion 27 of the housing 2. The upper portion of the deformable portion 31 has a columnar shape whose outer diameter is substantially equal to the diameter of the tube hole 27a of the pipe fitting portion 27. Further, the top surface 31a is a flat surface perpendicular to the in the axial direction of the deformable portion 31, and is exposed from the pipe fitting portion 27 (the pipe connecting port 6).

The lower portion of the deformable portion 31 where the bottom surface 31b is formed has a columnar shape whose diameter is larger than that of the upper portion of the deformable portion 31. The outer diameter of the lower portion of the deformable portion 31 is substantially equal to the diameter of the tubular portion 24 of the housing 2. Further, a recessed portion 34 is formed in the bottom surface 31b of the deformable portion 31, wherein the recessed portion 34 curves so as to recess toward the side of the top surface 31a.

The slit 33 reaches from the top surface 31a to the bottom surface 31b, and is linearly formed so as to pass through the axis of the deformable portion 31. In other words, the slit 33 is linearly formed so as to extend in the radial direction of the deformable portion 31. The length of the slit 33 is smaller than the diameter of the top surface 31a.

In a state where there is no pressing force applied on the top surface 31a, the slit 33 is in a closed state. Thus, in the state where there is no pressing force applied on the top surface 31a, the pipe connecting port 6 is blocked by the valve 3. On the other hand, if there is a pressing force applied on the top surface 31a and thereby the deformable portion 31 elastically deforms, two inner surfaces 31d which define the slit 33 will deform to rotate respectively in a clockwise direction and in a counterclockwise direction from the axis (i.e., to extend radially with respect to the axis), so as to face the flow path 13 of the housing 2. Similarly to the inner surfaces 31d, the top surface 31a of the valve 3 deforms to rotate with respect to the axis, so as to form an opening 36 (see FIG. 4C) that communicates with the flow path 13.

The fixing piece 32 is continuous with the outer peripheral surface 31c of the deformable portion 31 on the side of the lower portion, and is formed in a ring-like shape protruding outward in the radial direction of the deformable portion 31. The fixing piece 32 has two flat surfaces 32a, 32b opposite to each other in the axial direction of the deformable portion 31. The flat surface 32a of the fixing piece 32 abuts the other end of the pipe fitting portion 27 of the housing 2, and the flat surface 32b of the fixing piece 32 abuts the one end of the tubular portion 24 of the housing 2.

Next, the dimensions of the valve 3 will be described below.

It is preferred that the diameter A of the upper portion of the deformable portion 31 is within a range of 3 to 5 mm (see FIG. 3). If the diameter A is smaller than 3 mm, the upper portion of the deformable portion 31 will enter the hole of the pipe 100 (see FIG. 4), so that the valve 3 will not elastically deform to open the slit 33.

Incidentally, the diameter A of the upper portion of the deformable portion 31 does not have to be substantially equal to the diameter X of the tube hole 27a of the pipe fitting portion 27. For example, in the case where the upper portion of the deformable portion 31 is formed in a taper shape whose diameter becomes larger as it goes toward the top surface 31a, the diameter of the top surface 31a is larger than the diameter X of the tube hole 27a of the pipe fitting portion 27. While in the case where the upper portion of the deformable portion 31 is formed in a taper shape whose diameter becomes smaller as it goes toward the top surface 31a, the diameter of the top surface 31a is smaller than the diameter X of the tube hole 27a of the pipe fitting portion 27.

Further, the tube hole 27a of the pipe fitting portion 27 may also be formed in a taper shape whose diameter is continuously reduced as it goes toward the flow path 13. With such a configuration, the closing property of the slit 33 of the valve 3 before being elastically deformed can be improved.

Here, the distance between the outer peripheral surface of the upper portion of the deformable portion 31 and the outer peripheral surface of the fixing piece 32 is defined as "distance b", and the distance between the outer peripheral surface of the lower portion of the deformable portion 31 and the outer peripheral surface of the fixing piece 32 is defined as "distance c". Further, the distance between the top surface 31a of the deformable portion 31 and the flat surface 32a of the fixing piece 32 is defined as "distance d". In order to reliably fix the valve 3 to the housing 2, it is preferred that the distances b, c, and d are equal to or larger than 0.5 mm.

The outer diameter L of the fixing piece 32 is preferably in a range of 5 to 7 mm. If the outer diameter L is too large, the outer diameter of the housing 2 has to be set large, so that there is a possibility that the screw portion 27c of the pipe fitting portion 27 can not be made into a size that fits the lock portion (the luer lock) of the pipe 100. While if the outer diameter L is too small, the opening property of the valve 3 while elastically deforming will become worse. Further, since the deformation amount of the valve 3 in the longitudinal direction becomes larger, the fixing property of the valve 3 with respect to the housing 2 will become worse.

Further, it is preferred that the length e of the slit 33 is within a range of 1 to 4 mm (see FIG. 2). If the length e of the slit 33 is too small, the opening property of the valve 3 while elastically deforming will become worse. While if the length e of the slit 33 is too large, the pipe 100 (see FIG. 4) will enter the slit 33.

In the present embodiment, the diameter A of the upper portion of the deformable portion 31 is set to about 4.1 mm, and the diameter of the lower portion of the deformable portion 31 is set to about 5.1 mm. Further, the height (i.e., the length in the axial direction) of the deformable portion 31 is set to 3 mm, and the depth of the recessed portion 34 of the bottom surface 31b is set to about 0.7 mm. In other words, the thickness of the central portion of the deformable portion 31 is about 2.3 mm.

Incidentally, in order for the valve 3 to elastically deform so that the top surface 31a forms the opening 36 which communicates with the flow path 13, the thickness of the central portion of the deformable portion 31 is preferably equal to or less than 4.0 mm.

Further, the outer diameter L of the fixing piece 32 is set to about 6.2 mm, and the thickness of the fixing piece 32 is set to about 0.7 mm, so that the fixing piece 32 is to be pressed by the one end of the tubular portion 24 and the other end of the pipe fitting portion 27 so as to be crushed to about 0.15 mm.

Incidentally, it is preferred that the compressibility of the fixing piece 32 is equal to or higher than 50%.

[Connection Between Connector and Pipe]

Figure 4:
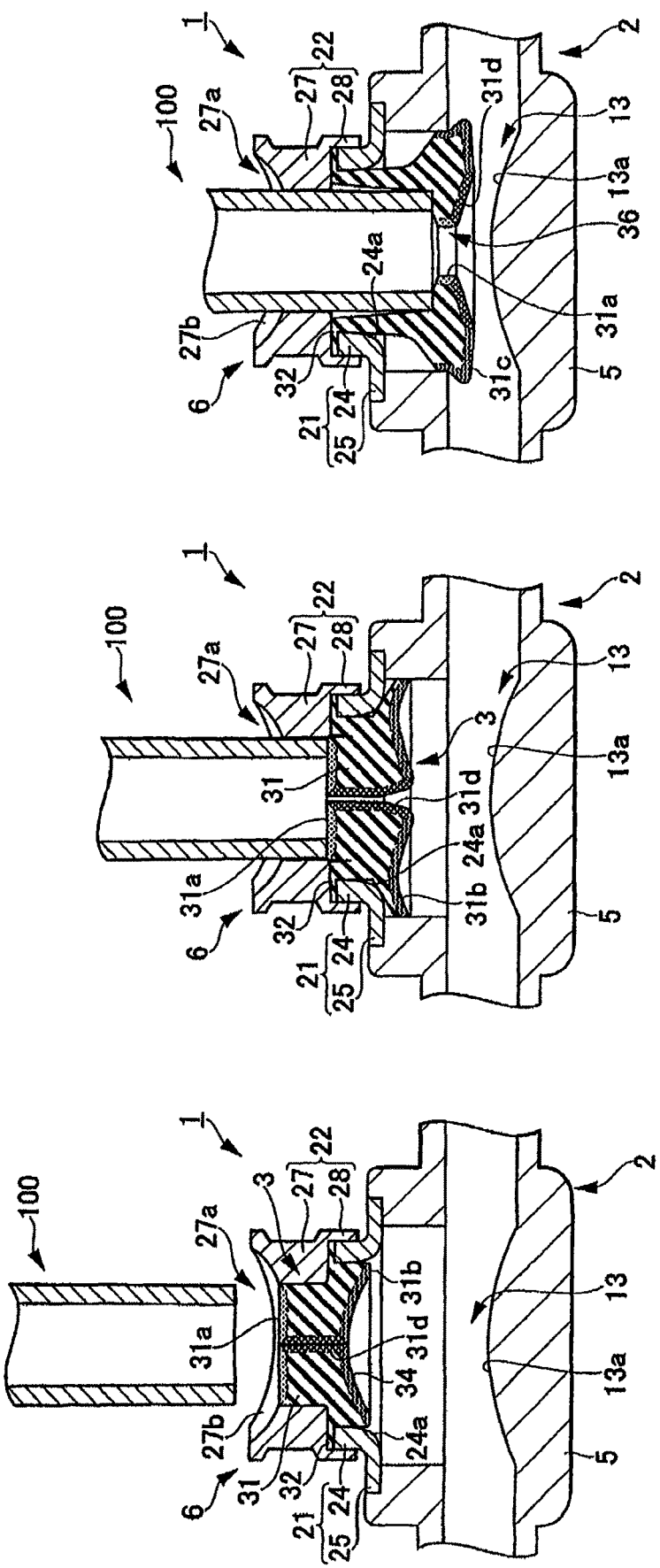

Next, the connection between the connector 1 and the pipe 100 will be described below with reference to FIG. 4.

FIG. 4A is a cross-sectional view showing a state in which the pipe is caused to face the connector 1. FIG. 4B is a cross-sectional view showing a state in which the top surface 31a of the valve 3 of the connector 1 is pressed by the pipe. FIG. 4C is a cross-sectional view showing a state in which the pipe 100 is connected to the connector 1.

As shown in FIGS. 4A to 4C, the pipe 100 is a portion or an instrument connected to the pipe connecting port 6 of the connector 1. Examples of the pipe 100 include a portion of a syringe (an injection device) to be connected by a needle tube, a pipe-like instrument (such as a luer taper member, a sheath or the like), and the like.

To connect the pipe 100 to the connector 1, first, the tip end of the pipe 100 is caused to face the pipe connecting port 6 of the connector 1 (see FIG. 4A). The diameter of the pipe 100 is continuously reduced as it goes toward the tip end, so that the pipe 100 can be liquid-tightly fitted to the pipe fitting portion 27 of the pipe connecting port 6.

Next, the tip end of the pipe 100 is inserted into the tube hole 27a of the pipe fitting portion 27 so as to press the top surface 31a of the deformable portion 31 of the valve 3 (see FIG. 4B). Incidentally, in the case where the pipe 100 has a lock portion, a screw portion of the lock portion is screwed onto the screw portion 27c of the pipe fitting portion 27. The tip end of the pipe 100 presses the top surface 31a of the valve 3, and thereby the deformable portion 31 of the valve 3 elastically deforms, so that the upper portion sinks to the side of the lower portion. Further, the upper portion expands outward in the radial direction, and enters the through-hole 15 of the housing 2.

At this time, the top surface 31a of the valve 3 abuts the tip end face of the pipe 100. Further, the inner surfaces 31d of the valve 3 deforms so as to rotate with respect to the axis of the valve 3 while being displaced relatively downward due to the downward elastic deformation of the deformable portion 31, so that the slit 33 is opened. Further, the bottom surface 31b of the valve 3 is pressed and expanded toward the side of the inner surface which defines the through-hole 15 of the housing 2.

Further, when the tip end of the pipe 100 is inserted into the tube hole 27a of the pipe fitting portion 27, the tip end of the pipe 100 is liquid-tightly fitted to the pipe fitting portion 27, and thereby the connection of the pipe 100 to the connector 1 is completed (see FIG. 4C). In such a state, the tip end face and a part of the outer peripheral surface of the pipe 100 are brought into liquid-tight contact with the elastically deformed deformable portion. Thus, liquid tightness between the connector 1 and the pipe 100 can be reliably ensured.

In the state where the connection of the pipe 100 to the connector 1 has been completed, the inner surfaces 31d of the valve 3 has deformed to rotate with respect to the axis so as to face the flow path 13 of the housing 2, while the bottom surface 31b has rolled back toward the lateral side of the valve 3. Further, the top surface 31a of the valve 3 has rotated so as to form two surfaces facing each other and parallel to the axis, so that the opening 36 which communicates with the flow path 13 of the housing 2 is formed.

As a result, the pipe 100 is brought into communication with the flow path 13 of the housing 2 by the opening 36 formed by the top surface 31a of the valve 3. Thus, the tip end of the pipe 100 can be prevented from entering the flow path 13. With such a configuration, the tip end of the pipe 100 can be prevented from contacting the liquid in the flow path 13, and therefore the risk of the liquid in the flow path 13 being contaminated can be reduced.

Further, the path extending from the tip end of the pipe 100 to the flow path 13 of the housing 2 is equal to the length of the opening 36 formed by the top surface 31a. Thus, the path extending from the tip end of the pipe 100 to the flow path 13 can be reduced, and thereby the liquid can be prevented or hindered from being accumulated in the valve 3.

In other words, with the connector 1, not only the pipe 100 can be prevented from entering the flow path 13, but also the liquid can be prevented or hindered from being accumulated in the valve 3.

Further, in the connector 1, the curved surface 24a is formed in the inner surface of the tubular portion 24 of the pipe connecting port 6. Thus, when the top surface 31a of the valve 3 is pressed, the deformation of the lower portion of the valve 3 can be guided by the curved surface 24a. As a result, not only the bottom surface 31b can be reliably rolled back toward the lateral side of the valve 3, but also the inner surfaces 31d can be reliably caused to face the flow path 13 of the housing 2.

Further, if the curved surface smoothly continues to reach the flow path 13, the valve 3 will form the opening 36 while deforming along the curved surface. Thus, it is unlikely that a gap will be generated between the valve 3 and the pipe connecting port 6, and therefore liquid (drug) can be prevented or hindered from being accumulated.

To remove the pipe 100 from the connector 1, the pipe 100 is pulled from the pipe fitting portion 27, so that the valve 3 is released from the pressure of the tip end of the pipe 100, and restored to the state where the pipe connecting port 6 is blocked (see FIG. 4A). In the state where the pipe connecting port 6 is blocked, since the bottom surface 31b of the valve 3 is provided with the recessed portion 34, the thickness of the valve 3 can be reduced, so that when connecting the pipe 100, the valve 3 becomes easy to deform.

In the present embodiment, the valve 3 elastically deforms so that the entire top surface 31a forms the opening 36 which communicates with the flow path 13 of the housing 2. However, the present invention also includes a configuration in which the valve deforms so that a portion of the top surface is rolled back to form the opening which communicates with the flow path, and the other portion liquid-tightly abuts the tip end face of the pipe 100.

Further, in the present embodiment, the upper portion and the lower portion of the deformable portion 31 of the valve 3 have different diameters; however, the upper portion and the lower portion of the deformable portion of the present invention may also have the same diameter.

2. Second Embodiment

Next, a connector according to a second embodiment of the present invention will be described below with reference to FIG. 5.

FIG. 5 is a perspective view showing a valve of the connector according to the second embodiment of the present invention.

The connector of the second embodiment has the same configuration as that of the connector 1 of the first embodiment. The connector of the second embodiment differs from the connector 1 of the first embodiment in a valve 43 only. Thus, herein the description will focus on the valve 43.

[Valve]

As shown in FIG. 5, the valve 43 is formed in the same shape as the valve 3 of the first embodiment, and has a cross-shaped slit 45. The slit 45 consists of two linear slit portions 45a, 45b each extending in the radial direction of the deformable portion 31. The two linear slit portions 45a, 45b intersect at substantially 90 degrees. The point where the two linear slit portions 45a, 45b intersect coincides with the axis of the deformable portion 31.

In the valve 43 having the aforesaid configuration, when the top surface 31a is pressed, the inner surfaces will deform to rotate with respect to the axis so as to face the flow path 13 of the housing 2, while the bottom surface 31b will roll back toward the lateral side of the valve 43. Further, the top surface 31a of the valve 43 will rotate to form two pairs of surfaces, each pair of surfaces facing each other and parallel to the axis, so as to form the opening 36 which communicates with the flow path 13 of the housing 2.

Thus, with the connector of the second embodiment, not only the pipe 100 can be prevented from entering the flow path 13, but also the liquid can be prevented or hindered from being accumulated in the valve 43.

Further, with the connector of the second embodiment, since the valve 43 is provided with the cross-shaped slit 45, the valve 43 can be caused to deform in a balanced manner, and the opening property after deformation can be improved. Further, since the opening property is improved, it is not necessary to insert the pipe 100 as deep as the conventional connectors, and therefore the valve is less susceptible to breakage.

Incidentally, in the present embodiment, the two slit portions 45a, 45b intersect at substantially 90 degrees; however, in the cross-shaped slit according to the present invention, the angle at which the two slit portions intersect can be arbitrarily set.

3. Third Embodiment

Next, a connector according to a third embodiment of the present invention will be described below with reference to FIGS. 6, 7A and 7B.

FIG. 6 is a perspective view showing a valve of the connector according to the third embodiment of the present invention. FIG. 7A is a plan view of the valve, and FIG. 7B is a bottom view of the valve.

Similar to the connector of the second embodiment, the connector of the third embodiment differs from the connector 1 of the first embodiment in a valve 53 only. Thus, herein the description will focus on the valve 53.

[Valve]

As shown in FIGS. 6, 7A and 7B, the valve 53 is formed in the same shape as the valve 3 of the first embodiment, and has a slit 55. The slit 55 consists of two linear slit portions 55a, 55b each extending in the radial direction of the deformable portion 31, and the two linear slit portions 55a, 55b intersect at substantially 90 degrees. The point where the two linear slit portions 55a, 55b intersect coincides with the axis of the deformable portion 31.

The slit portion 55a is formed to reach from the top surface 31a of the deformable portion 31 to the bottom surface 31b of the deformable portion 31. While the slit portion 55b is formed to reach from the bottom surface 31b of the deformable portion 31 to an intermediate portion of the deformable portion 31. In other words, the slit portion 55b does not reach the top surface 31a.

Thus, the slit 55 is formed linearly on the side of the top surface 31a of the deformable portion 31 (see FIG. 7A) and formed crosswise on the side of the bottom surface 31b of the deformable portion 31 (see FIG. 7B).

In the valve 43 having the aforesaid configuration, when the top surface 31a is pressed, the inner surfaces will deform to rotate with respect to the axis so as to face the flow path 13 of the housing 2, while the bottom surface 31b will roll back toward the lateral side of the valve 53. Further, the top surface 31a of the valve 53 will rotate to form two surfaces facing each other and parallel to the axis, so as to form the opening 36 which communicates with the flow path 13 of the housing 2.

Thus, with the connector of the third embodiment, not only the pipe 100 can be prevented from entering the flow path 13, but also the liquid can be prevented or hindered from being accumulated in the valve 53.

In the connector of the third embodiment, since the slit 55 is linearly formed on the side of the top surface 31a, pressure resistance when closed can be ensured. Further, since the slit 55 is formed crosswise on the side of the bottom surface 31b, the opening property after deformation can be improved.

Incidentally, in the present embodiment, the two slit portions 55a, 55b intersect at substantially 90 degrees; however, the angle at which the two slit portions intersect can be arbitrarily set.

It is to be understood that the present invention is not limited to the embodiments described above and shown in the drawings, and various modifications can be made without departing from the spirit and scope of the claims of the present invention. For example, in the aforesaid embodiments, the first member 21 of the pipe connecting port 6 is joined to the housing main body 5, and the second member 22 is joined to the first member 21 by fusion or the like. However, the pipe connecting port according to the present invention may also have a configuration in which the first member is sandwiched by the second member and the housing main body, and the second member is joined to the housing main body 5 by fusion or the like.

Further, in the aforesaid embodiments, the deformation of the lower portion of the valve 3 is guided by the curved surface 24a provided in the tubular portion 24 of the pipe connecting port 6; however, the curved surface that guides the deformation of the lower portion of the valve may also be provided in the housing main body.

| Explanation of Reference Numerals | |
|---|---|
| 1 | connector |
| 2 | housing |
| 3, 43, 53 | valve |
| 5 | housing main body |
| 6 | pipe connecting port |
| 11 | first tube connecting port |
| 12 | second tube connecting port |
| 13 | flow path |
| 15 | through-hole |
| 16 | fitting recess |
| 21 | first member |
| 22 | second member |
| 24 | tubular portion |
| 24a | curved surface |
| 25 | flange portion |
| 27 | pipe fitting portion |
| 28 | connection piece |
| 31 | deformable portion |
| 31a | top surface |
| 31b | bottom surface |
| 31c | outer peripheral surface |
| 31d | inner surface |
| 32 | fixing piece |
| 33, 45, 55 | slit |
| 34 | recessed portion |
| 36 | opening |
| 45a, 45b, 55a, 55b | slit portion |
| 100 | pipe |

The invention claimed is:

1. A connector configured to connect a pipe of a medical product to a flow path in a liquid-tight manner so that an interior of the pipe is in fluid communication with the flow path, the connector comprising:
a housing having the flow path through which a liquid passes, and a substantially circular pipe connecting port which communicates with the flow path;
a valve formed of an elastic material and adapted to block the pipe connecting port of the housing,
wherein the valve comprises:
a columnar deformable portion having a top surface exposed from the pipe connecting port, a bottom surface opposite to the top surface, and a slit extending from the top surface to the bottom surface, the columnar deformable portion possessing a central axis, the columnar deformable portion including a bottom end part that includes the bottom surface; and
a ring-shaped fixing piece protruding from an outer peripheral surface of the columnar deformable portion, in an intermediate portion between the top surface and the bottom surface, and fixed to the housing, and
the housing possessing an inner surface, the inner surface of the housing comprising an outwardly expanded inner surface portion that expands outwardly in a direction away from the central axis of the columnar deformable portion so that a distance between the outwardly expanded inner surface portion and the central axis of the columnar deformable portion increases at closer axial distances to the flow path, the outer peripheral surface of the bottom end part of the columnar deformable portion being spaced from the outwardly expanded inner surface portion before the top surface of the columnar deformable portion is pressed by the pipe so that a space exists between the outer peripheral surface of the bottom end part of the columnar deformable portion and the outwardly expanded inner surface portion of the housing, a part of the columnar deformable portion moving into contact with the outwardly expanded inner surface portion of the housing as the columnar deformable portion elastically deforms during movement of the pipe towards the flow path.

2. The connector according to claim 1, wherein the bottom surface of the columnar deformable portion includes a recessed portion that is curved so that a center of the recessed portion that is curved is at the slit and so that the recessed portion curves away from the top surface of the coolumnar deformable portion at increasing distances radially outwardly from the center of the recessed portion.

3. The connector according to claim 1, wherein the slit is a linearly extending slit.

4. The connector according to claim 1, wherein the slit is a cross-shaped slit.

5. The connector according to claim 1, wherein the slit is linearly shaped at the top surface and is cross-shaped at the bottom surface so that the slit possesses a shape at the top suface that is different from the shape of the slit at the bottom surface.

6. The connector according to claim 1, wherein the outwardly expanded inner surface portion of the housing comprises a curved surface which guides the elastic deformation of the valve so that at least a portion of the bottom surface of the columnar deformable portion rolls back laterally outwardly.

7. The connector according to claim 6, wherein the curved surface smoothly continues to reach the flow path.

8. The connector according to claim 1, wherein the pipe connecting port has a pipe fitting portion configured to receive the pipe when the pipe is pressed against the top surface of the columnar deformable portion and is moved toward the flow path, the columnar deformable portion including an upper portion between the ring-shaped fixing piece and the top surface, the upper portion of the columnar deformable portion being in direct contact with the pipe fitting portion before the pipe is moved towards the flow path and being moved out of contact with the pipe fitting portion as the pipe is moved towards the flow path.

9. The connector according to claim 8, wherein an outer peripheral surface of the pipe fitting portion is provided with a screw portion to be screwed with a lock portion formed around the pipe at a predetermined interval.

10. The connector according to claim 1, wherein, when the pipe is liquid-tightly fitted to the pipe connecting port, a tip end face of the pipe contacts the elastically deformed columnar deformable portion and an outer peripheral surface of the pipe immediately adjacent the tip end contacts the elastically deformed columnar deformable portion.

11. The connector according to claim 1, wherein, when the pipe is liquid-tightly fitted to the pipe connecting port, a tip end of the pipe does not enter the flow path.

12. The connector according to claim 1, wherein, when the pipe is liquid-tightly fitted to the pipe connecting port, a lower end portion of the elastically deformed columnar deformable portion is located closer to the flow path than a tip end face of the pipe.

13. The connector according to claim 1, wherein when the top surface of the columnar deformable portion is pressed by the pipe, the columnar deformable portion elastically deforms so that the bottom surface of the columnar deformable portion rolls back laterally outwardly, and at least a portion of the bottom surface contacts an inner face of the housing.

14. A method of connecting a pipe of a medical product to a flow path in a housing in a liquid-tight manner, the method comprising:
inserting an end portion of the pipe, including a tip end of the pipe, into a pipe connecting port of the housing, the pipe connecting port opening into the flow path, and including a valve fixed in place in the pipe connecting port, the valve being formed of elastic material allowing a deformable portion of the valve to elastically deform when the tip end of the pipe is pressed against a first end surface of the deformable portion which faces away from the flow path in the housing, the valve also comprising a slit extending completely through the valve so that the slit opens to the first end surface of the deformable portion and to an oppositely facing second end surface of the deformable portion, with inner surfaces of the deformable portion on opposite sides of the slit facing one another, the housing possessing an inner surface comprising an outwardly expanded inner surface portion that expands outwardly in a direction away from a central axis of the the deformable portion so that the outwardly expanded inner surface portion is spaced greater distances from the central axis of the columnar deformable portion at closer axial distances to the flow path, the deformable portion being spaced from the outwardly curved inner surface of the housing;
pressing the tip end of the pipe, which has been inserted into the pipe connecting port, into contact with the first end surface of the deformable portion in a direction towards the flow path;
moving the pipe toward the flow path so that a part of the deformable portion moves from a position spaced from the outwardly expanded inner surface portion of the housing to a position in contact with the outwardly expanded inner surface portion of the housing as the deformable portion deforms during movement of the pipe towards the flow path; and
completing connection of the pipe to the flow path in the housing such that the interior of the pipe is in fluid communication with the flow path through an opening in the valve while the tip end of the pipe is in liquid-tight contact with a part of the first end surface of the valve and while an outer peripheral surface of the pipe immediately adjacent the tip end is in liquid-tight contact with the deformable portion.

15. The method according to claim 14, wherein the valve includes a fixing piece by which the valve is fixed in place in the pipe connecting port, and the deformable portion including a lower portion below the fixing piece, the lower portion possessing a first outer diameter before the pressing of the tip end of the pipe into contact with the first end surface of the deformable portion, and upon the completing of the connection of the pipe to the flow path, a part of the deformable portion of the valve which has deformed expands outwardly and possesses an outer diameter greater than the first outer diameter.

16. The method according to claim 14, wherein the pipe connecting port possesses first and second ends at opposite axial ends of the pipe connecting port, further comprising a fixing portion that protrudes outwardly from an outer peripheral surface of the deformable portion, the fixing portion being held in place by a portion of the pipe connecting port located intermediate the first and second ends of the pipe connecting port.

17. The method according to claim 16, wherein the first end of the pipe connecting port is located closer to the flow path than the second end, an axial distance between the first end of the pipe connecting port and the portion of the pipe connecting port at which the fixing portion is held in place being related to the deformable portion so that upon the completing of the connection of the pipe to the flow path, the deformed deformable portion extends axially beyond the first end of the pipe connecting port and expands radially outwardly.

* * * * *